United States Patent
Sheynkman

(10) Patent No.: US 9,897,511 B2
(45) Date of Patent: Feb. 20, 2018

(54) CAN GROWTH/BUCKLING TESTER

(71) Applicant: Jacob Yefim Sheynkman, Brooklyn, NY (US)

(72) Inventor: Jacob Yefim Sheynkman, Brooklyn, NY (US)

(*) Notice: Subject to any disclaimer, the term of this patent is extended or adjusted under 35 U.S.C. 154(b) by 85 days.

(21) Appl. No.: 14/828,800

(22) Filed: Aug. 18, 2015

(65) Prior Publication Data
US 2016/0258835 A1    Sep. 8, 2016

Related U.S. Application Data

(60) Provisional application No. 62/126,713, filed on Mar. 2, 2015.

(51) Int. Cl.
| | |
|---|---|
| *G01M 3/36* | (2006.01) |
| *G01M 3/32* | (2006.01) |
| *G01N 3/00* | (2006.01) |
| *G01M 99/00* | (2011.01) |
| *G01N 33/00* | (2006.01) |

(52) U.S. Cl.
CPC .......... *G01M 3/363* (2013.01); *G01M 3/3281* (2013.01); *G01M 3/36* (2013.01); *G01M 99/00* (2013.01); *G01N 3/00* (2013.01); *G01N 2033/0081* (2013.01)

(58) Field of Classification Search
CPC ........ G01M 3/10; G01M 3/36; G01M 3/3281; G01M 3/363
See application file for complete search history.

(56) References Cited

U.S. PATENT DOCUMENTS

| | | | | |
|---|---|---|---|---|
| 3,675,321 A | * | 7/1972 | Arel | B67B 7/38 30/404 |
| 4,194,388 A | * | 3/1980 | Mack | G01M 3/36 73/37 |
| 4,555,935 A | * | 12/1985 | Elert | G01N 3/12 73/37 |
| 5,123,278 A | * | 6/1992 | McKittrick | G01N 3/12 73/49.3 |

FOREIGN PATENT DOCUMENTS

| | | | | |
|---|---|---|---|---|
| JP | 06200910 A | * | 7/1994 | |
| JP | 2013217647 A | * | 10/2013 | F28F 3/083 |

* cited by examiner

*Primary Examiner* — Daniel J Colilla

(57) ABSTRACT

The growth/buckle tester relates to a device for testing strength of metal cans. Using the position of the can on top of Belleville spring and expandable rubber bushing, holding by sectional clamps with turning cams and middle central part from outside, permitted create uniform holding and clamping force in horizontal direction. Using chamfers on holding plates and turning cams for holding the testing can vertically create necessary space around the stand for growth/buckle tests. The chamber created inside the can with almost the same volume of volume of air for the test reducing dispersion of measurement values. Cuts around of Bellville spring make path for delivering testing air pressure for the growth/buckle tests. Angle of rotation turning cams depend and control by outside diameter of testing can.

7 Claims, 5 Drawing Sheets

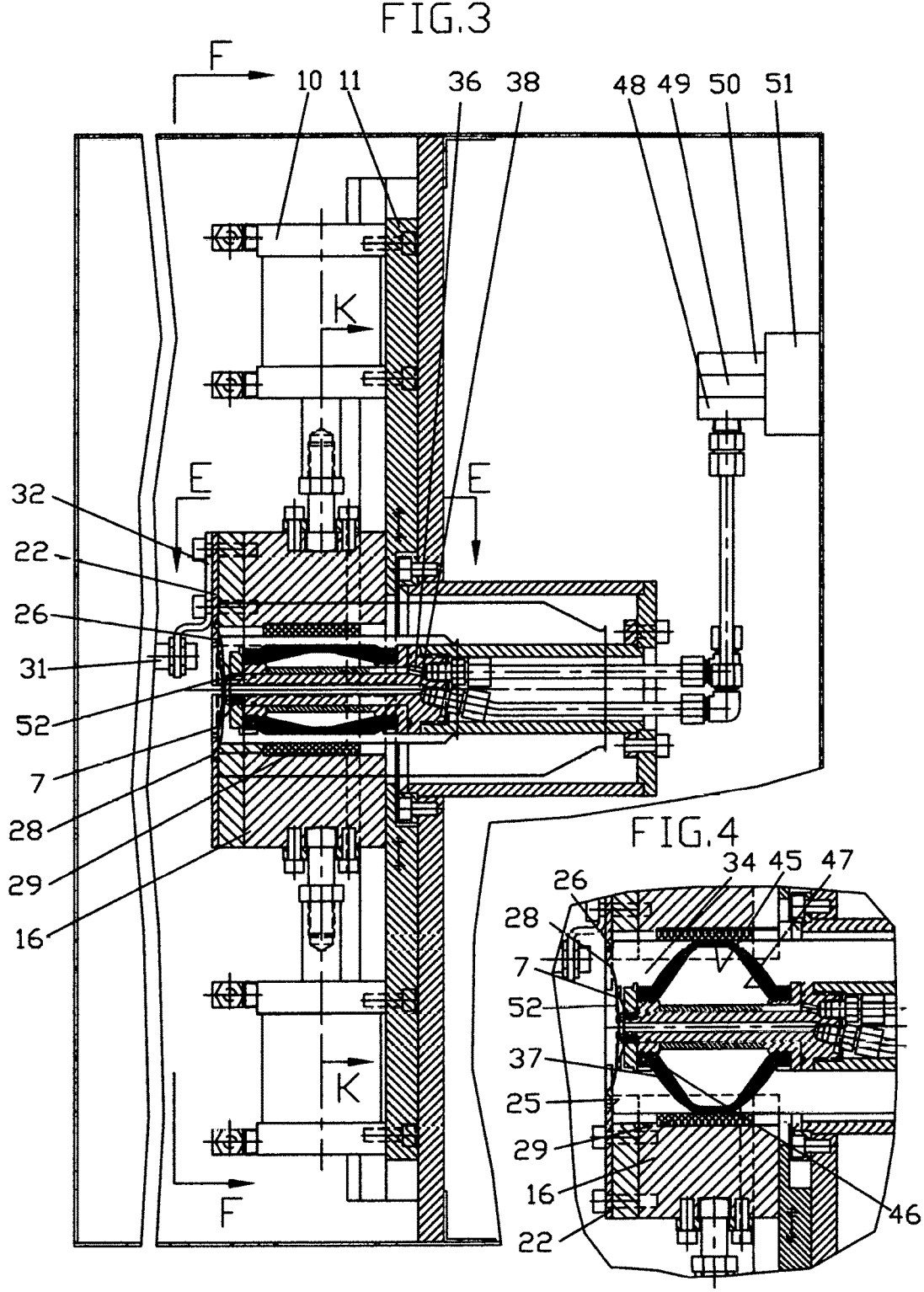

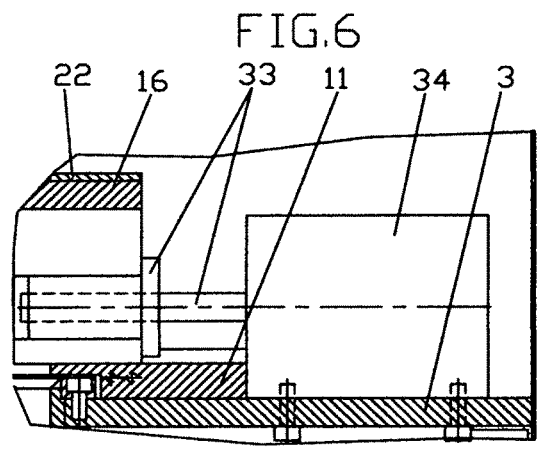
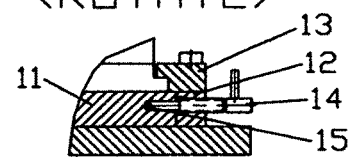
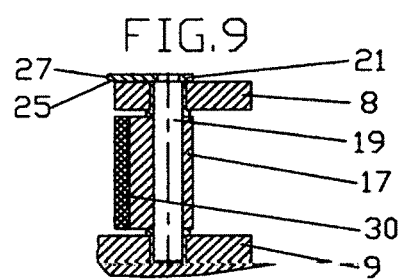
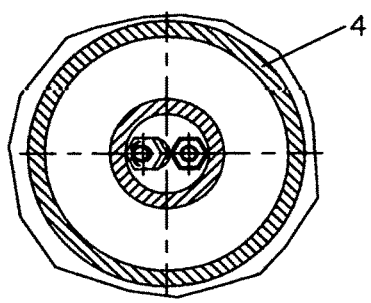
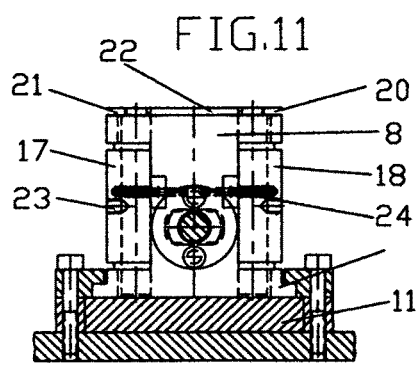
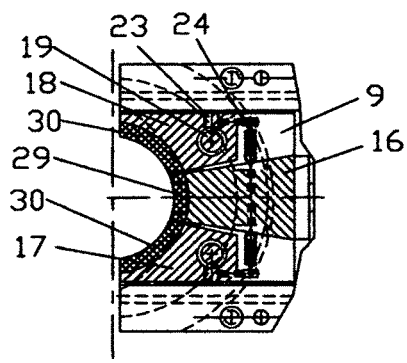
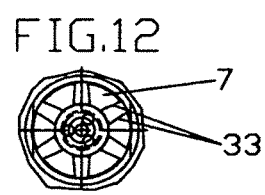

CAN GROWTH/BUCKLING TESTER

TECHNICAL FIELD

The present invention is generally directed to quality control test equipment and products designed to perform tests on a variety of beverage can types. More particularly, the present invention is directed to can/end growth and buckling testers.

BACKGROUND OF THE INVENTION

The current invention related to a device for testing the strength of metal cans. Specifically, for testing growth and buckling strength of closed end of the metal can. Conventionally testers for buckling tests make separately for group beverage cans separated by diameters and heights. All sizes of the cans have in common the same diameter of the open neck, therefore in majority of testers the can based, hold, clamp and seal in neck area during test. Some testers base on internal surface of the close end of the can, seal the can from inside and clamp from outside base on internal and external walls of the can. Because each size of the can has different diameter and height, each tester supposed to have many sets of holding, clamping and sealed parts. Because the can hold by friction only, therefore the can has possibility to slide in vertical direction during the test under buckle pressure and need additional support (as an example—the knurling) to the sides clamps for perform growth test. This create danger of penetration the knurling inside the thin-walled can and tear inflated testing can, before test will be finish, Testers, using hollow needles for pressurizing can, create additional pressure on wall of the can during penetration, deform the can, the hollow needle do not sealed and therefore leak of air affect tolerance of the test result. Different height of the cans, sliding during test, different deformation under pressure of hollow needle penetration, different volume of the air needed for inflation increase dispersion of measurement values.

Majority of growth testers at present are separate products, because cans have to hold vertically without any motion in vertical direction to determine growth under certain amount of pressure. Each different can has different height and diameter but holding at the neck of the can, therefore the volume of air is, holding parts are different, requiring air accumulators for quick compensation of volume of air and installation of measurement equipment requiring manual job. Differences of nature of tests create differences in equipment for buckle and growth tests. New line of growth/buckle testers at present design as combination of buckle testers with additional growth unit, install on top of buckle testers. Because all sizes of cans have the same diameter of the neck, and different diameters of the body, they cannot test cans without additional parts for performing growth test. Typical can end testers represent and illustrated in U.S. Pat. Nos. 4,194,388, 4,555,935, 5,123,278, as well as testers manufactured and sold by Altek Company, Torrington, Conn., buckle tester Model 9009G and growth/buckle testers Model 9009F2, Sencon Inc., Bedford Park, Ill., buckle tester Model SI6110 with additional module 516115 for growth test, CMC-Kuhnke Inc., Albany, N.Y., Model DRT-3000 for growth/buckle tests.

BRIEF DESCRIPTION OF THE DRAWINGS

In the drawings:

FIG. 3 is a sectional view D-D along lines D-D on FIG. 2, showing based plates with installed slides with top holding plates for hold the tested can during the tests, cylinders sectional clamps and holes for air delivery for inflation expandable rubber bushing and growth/buckling tests, sensor for determine maximum and residual growth.

FIG. 4 is a sectional view D-D along lines D-D on FIG. 2, showing based plates with installed slides with top holding plates for hold tested can during the tests, cylinders and holes for air delivery with inflated to maximum diameter of the can expandable rubber bushing and growth/buckling tests, sensor for determine maximum and residual growth.

FIG. 6 is a sectional view D-D along lines D-D on FIG. 2 for option using motorize lead screw for movement of sectional clamps with top holding plates.

FIG. 7 is a sectional view H-H along lines H-H on FIG. 4 showing option with guides used for motorize lead screws as activators.

FIG. 8 is a sectional view H-H along lines H-H on FIG. 4 showing option with guides and retractable spring plungers used for cylinders as activators.

FIG. 9 is a sectional view G-G along lines G-G, on FIG. 5 showing pin for locate and rotate turning cams.

FIG. 10 is a sectional view C-C along lines C-C on FIG. 2 showing tubing for air delivery for inflation and tests.

FIG. 11 is a sectional view E-E along lines E-E on FIG. 3 showing sectional clams with turning cams and top holding plates.

FIG. 12 is a sectional view B-B along lines B-B on FIG. 2 showing Bellville spring use for support the testing can from inside and with slots for air delivery for tests.

FIG. 13 is a sectional view K-K along lines K-K showing turning cams with rubber plates and body of sectional clamp.

SUMMARY OF INVENTION

This unique design, with placing and positioning the can on inside the dome area of the can on top of Belleville spring and hold the tested can in fixed position from the top of the tested can, and air pressure push the testing can to the same direction as Belleville spring do. This placement of the testing can allow make growth/buckle tests for testing all currently producing cans with variation of height, does not have any additional replaceable parts, units (such as cylinders) and holding parts for holding testing cans during testing different diameters and height of testing cans as current designs do. Combination of mechanical properties of rubber, variation of thickness of the internal wall of the rubber bushing and the durometer of rubber allow create chamber between expandable rubber bushing and testing can for any diameters of the all currently producing cans, which hold testing pressure and therefore do not need extra parts for sealed the inside the testing can and hold testing pressure during the test.

The chamber with almost the same volume created by this unique design for any testing can, method of placing of testing can, needless air accumulators for quickly compensation differences of volume of the air for different size of cans, reducing time of the test and reducing dispersion of measurement values, as current designs do, make test more accurate. Outside movable rubber plates are contacted the can during the test, partially absorb inflated pressure and relief thin-walled tested can from the pressure, increase reliability and safety during test.

Each holding clamps include three separate parts: middle part is fixed and have top holding plate which attached to body of the holding clamp and attached rubber plate, which contact wall of the testing can. Side parts include sectional turning cams with top holding plates, which tuning with cams. Rubber plates attached to sectional turning cams able to contact the can any diameter around during the test, partially absorb inflated pressure and relief thin-walled tested can from the pressure, increase reliability and safety during test. The angle of rotation of sectional turning cams control by contacting the testing can. The top outside area of the testing can contact with top holding plates, install to sectional turning cams by outside wall and chamfers located on the top of sectional holding plates. Holding plates are pushing, stopping and holding testing can between holding plates and Belleville spring, edges of holding plates create necessary space around the stand area for tests. This is creating fixed vertical position of the testing can with open the stand area and the dome area, permitted make growth and buckle tests in one tester, but not in separate testers as current design do.

DETAILED DESCRIPTION OF ILLUSTRATED EMBODIMENT

Figure 1:
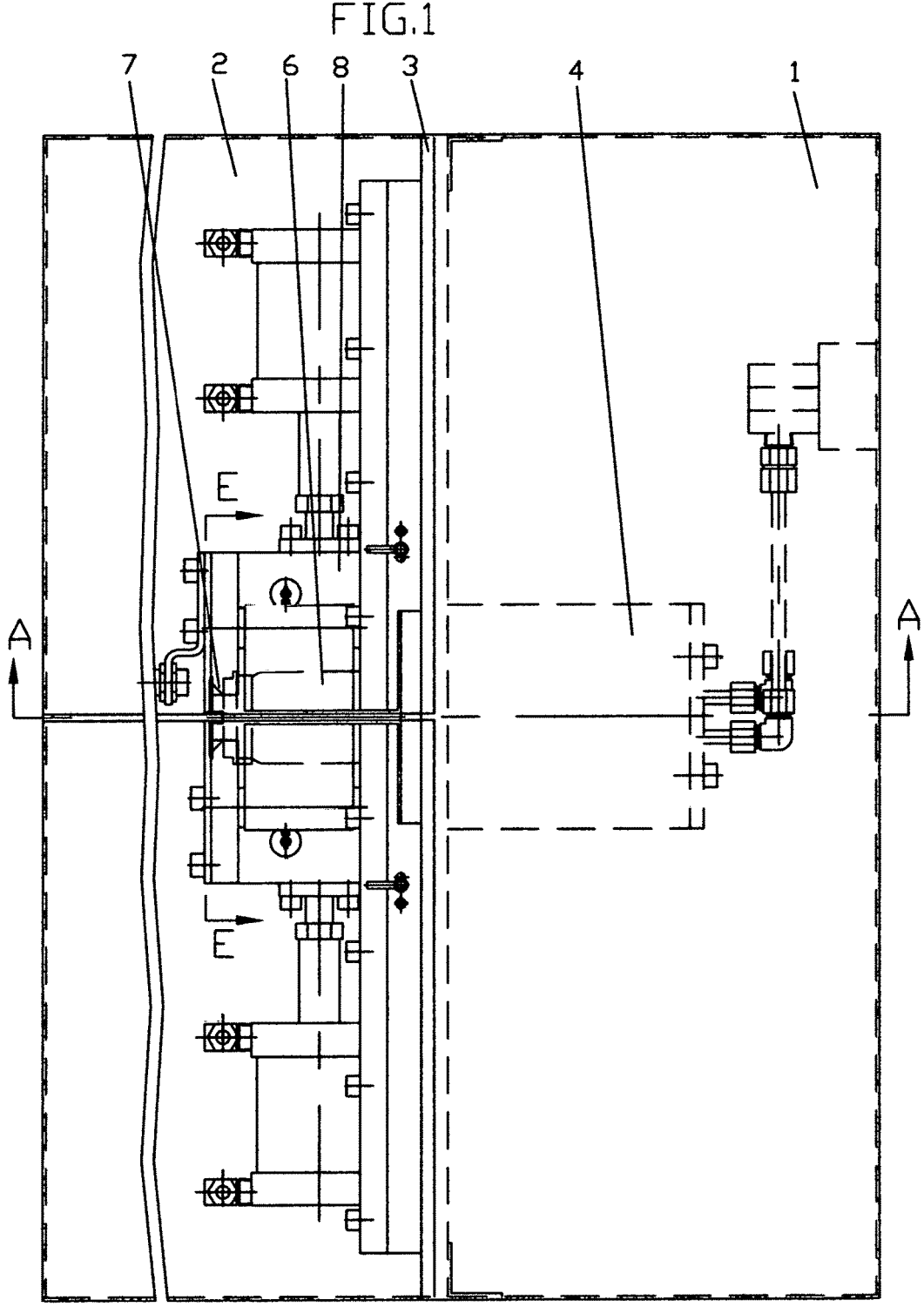
FIG. 1 is a front view of the growth/buckling tester showing from the closing doors with clear plastic windows, through windows sees intermediate plate with expandable rubber bushing, cylinders and bottom housing and valves, located in lower part of the tester.
Figure 2:
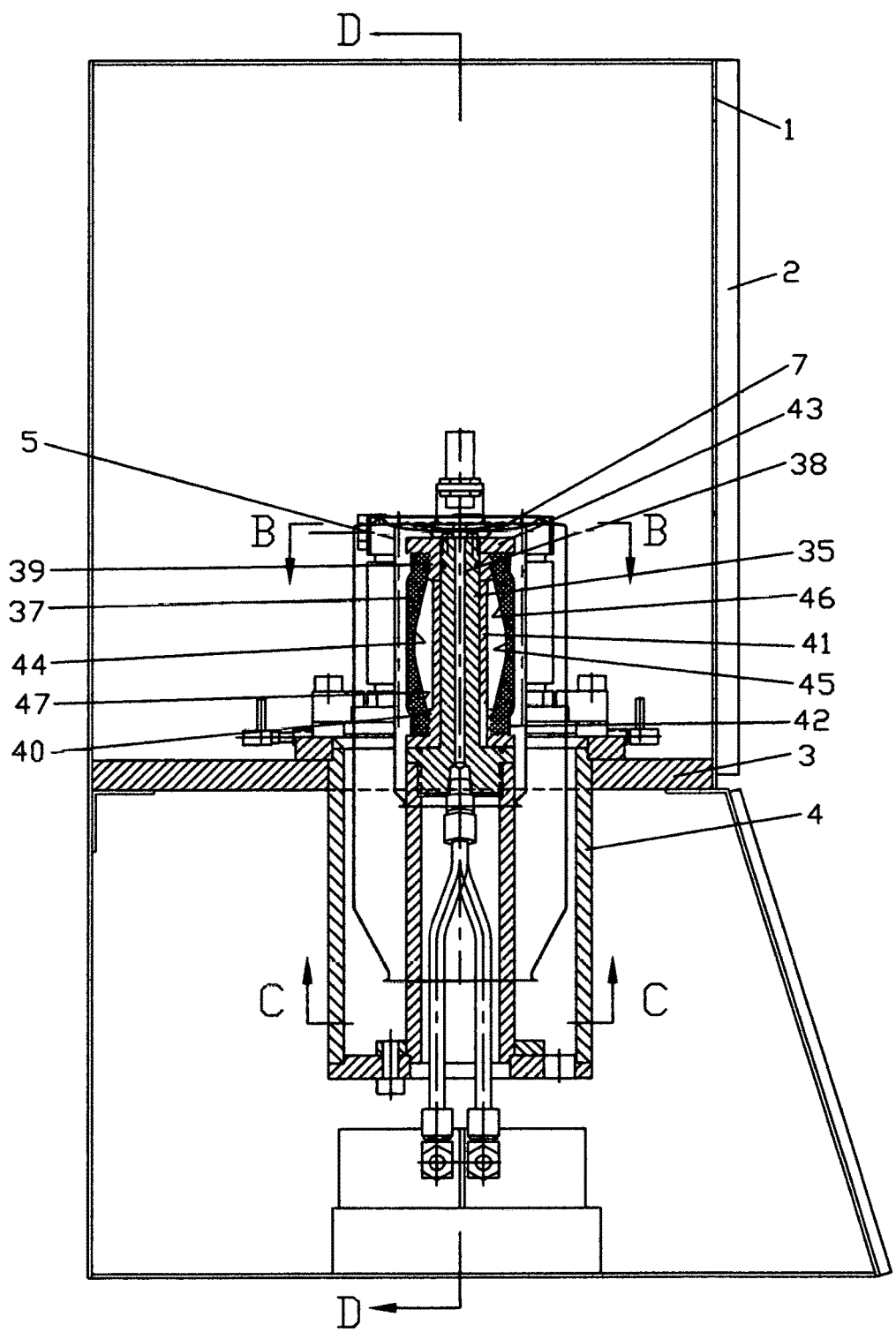
FIG. 2 is a sectional view A-A along lines A-A on FIG. 1, showing expandable bushing with air delivery hole for growth/buckling test, sensor determine for maximum and residual growth.
Figure 5:
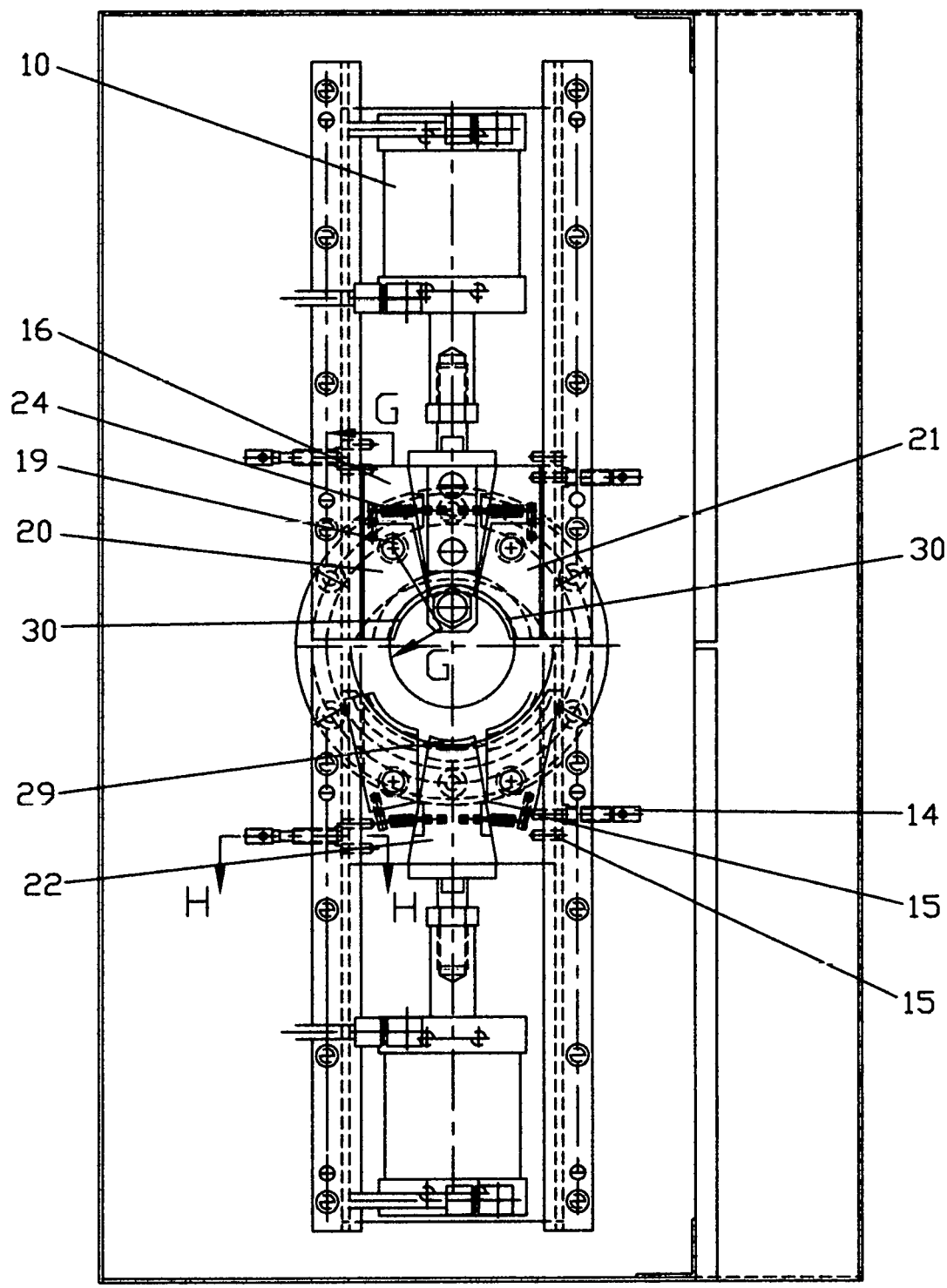
FIG. 5 is a sectional view F-F, along lines F-F on FIG. 3, showing top view of sectional clamps with top holding plates for positioning and holding the testing can during the tests, cylinders and guides, sensor for determine maximum and residual growth.

The growth/buckle tester consist (see FIGS. 1 and 2) of housing 1 with doors 2, intermediate plate 3 with installed on the middle flanged bushing 4 with depth which accepted any height of the currently producing cans 5, expandable plug 6 with Belleville spring 7 on top of plug 6. On opposite sides of the can 5 locate sectional clamps 8, which bottom plates 9 served as a slides. Cylinders 10 activate movement of sectional clamps 8, placed on based plates 11, guided and hold by guides 12 and 13. Retractable spring plungers 14 (see FIGS. 2, 5 and 8), determine differences between diameters of the testing cans 5 by engaging in holes 15 on base plates 11 and hold based plates 11 in position related to certain diameter of the testing can 5.

Sectional clamps 8 (see FIGS. 3, 4, 5, 9 and 11) consist three different parts: body 16 of sectional clamps 8 which presented as a I-beam and serve as a support for two turning cams 17 and 18, which connected with the body 16 by pins 19 with attached to them sides top holding plates 20 and 21. Middle top holding plates 22 install on top of bodies 16 of sectional clamps 8. Turning cams 17 and 18 (see FIGS. 5, 9, 11 and 13) connected to pins 19 by set screws 23. Each turning cam 17 and 18 connected with the bodies 16 by extension springs 24. Each top holding plated 20, 21 and 22 have chamfers 25 for pushing and holding testing can 5 at outside area 26 of the testing can 5 (see FIGS. 3, 4. and 11). Edges 27 of top holding plates 20, 21 and 22 create necessary space between edges of top holding plates 20, 21, 22 and the stand 28 of testing can 5 for growth/buckle tests.

On internal vertical surfaces of bodies 16 attached rubber plates 29. On vertical surfaces of turning cams 17 and 18 attached rubber plates 30. The rubber plates 29 and 30 contacted outside wall of the testing can 5. Bottom plate 9 of sectional clamps 8 serve as slides and have two different options.

On one side of top middle holding plate 22 (see FIGS. 1, 3 and 5) placed sensor 31 with bracket 32, which determine amount of growth the stand 28 of the testing can 5 under growth pressure, which always lower then buckling pressure.

First option (see FIGS. 3, 5 and 8) with actuators as cylinders 10 consist of retractable spring plungers 14 on guides 12 and engaging in holes 15 on based plates 11, which use to stop base plates 11 in positions related to differences between diameters of the testing cans 5 and hold based plates 11 during the tests. Bottom plates 9 of sectional clamps 8 guide and hold by guides 13. Sectional clamps 8 with top holding plates 20,21 and 22, turning cams 17 and 18 with rubber plates 29 and 30 actuate by cylinders 10 which have permanent stroke, which not depend from the diameters of testing cans 5.

The second option (see FIGS. 6 and 7) with actuators as motorize lead-screw consist of sectional clamps 8 with top holding plates 20, 21 and 22 with lead-screws 33 installed on base plates 11, guided and hold by guides 13, actuator step motors 34 installed directly to intermediate plate 3 and controlled by PLC (do not show), moved with sectional clamps 8 with bottom plates 9 as a slides and top holding plates 20, 21 and 22 to position related to different diameter of the testing cans 5 by programming.

Top holding plates 20,21 install on turning cams 17 and 18 (see FIGS. 3, 5, 9 and 11) turn toward vertical axe of the testing can 5 and contact together with middle holding plates 22 the outside area 26 by chamfers 25, push dome area 52 of the testing can 5 against Bellville spring 7, preventing the can 5 from motion vertically. Turning cams 17 and 18 contact testing can 5 by rubber plates 30 and rotate with pins 19 and top holding plates 20 and 21 toward center of the testing can 5. Angle of rotation turning cams 17 and 18 depend and control on outside diameter of testing can 5. Edges 27 of top holding plates 20,21 and 22 create around the stand 28 necessary space for tests. Bellville spring 7 has separate cuts 33 around the Bellville spring 7 (see FIG. 12). Those cuts 33 make path for delivering testing air pressure to closed chamber 34. Close chamber 34 create between inflated the expandable plug 6 and internal wall of the testing can 5.

The expandable plug 6 (see FIGS. 1, 2, 3 and 4) consists of metal core 35 with two holes for delivering air pressure: the hole 36 off side of the core 35 for inflation of expandable rubber bushing 37 for creating close chamber 34 and second hole 38 on the center of the core 35 for delivering air pressure for growth and buckle tests. Expandable rubber bushing 37 installs on two collars 39 and 40 between which placed bushing 41 and tight on collars 39 and 40 by two ear clamp rings 42. Assembled expandable rubber bushing 37 with collars 39 and 40, bushing 41 and ear clamp rings 42 put on core 35 and tight on the core 35 by nut 43. Expandable rubber bushing 37 has inside special profile of the wall 44 and durometer, which make central part 45 stretched under inflation in vertical and horizontal directions and contact the testing can 5 from inside. The upper 46 and lower 47 parts of the expandable rubber bushing 37 turn in opposite directions, upper 46 is up and lower 47 is down by inflation and expandable rubber bushing 37 hold testing pressure in this position. Contact between inside wall of the testing can 5 and inflated expandable rubber bushing 37 create inside close chamber 34 (see FIG. 4).

Through central hole 38 deliver air pressure, which push the outside area 26 of tested can 5 against chamfers 25 of top holding plates 20, 21 and 22. On top of the nut 43 install Belleville spring 7 for placing the testing can 5. Air pressure deliver by valve 48,49 and 50 installed on manifold 51 (see FIG. 3).

The growth/buckle tester operates in follows:

Doors 2 of housing 1 open and the testing can 5 place on top of Belleville spring 7 by the dome area 52 upside down and located inside flanged bushing 4. Cylinders 10 with sectional clamps 8 and turning cams 17 and 18 with top holding plates 20,21 and 22 located in rear position. Turning cams 17 and 18 open wide by extension springs 24. Doors 2 close and the test able to start.

For first option: Based plates 11 with sectional clamps 8 with top holding plates 20, 21 and 22 and cylinders 10 move manually in position related to testing diameter of the testing can 5 and fixed by retractable spring plungers 14.

For second option: Based plates 11 with sectional clamps 8 with top holding plates 20, 21, and 22 move mechanically by lead—screws 33 motorized by step motors 34 in position related to outside diameter of the testing can 5 by PLC (do not shown) and programming of motion.

For both options: Cylinders 10 are pushing sectional clamps 8 with bottom plates 9 used as the slides together with top holding plates 20, 21 and 22 toward center of the testing can 5 by pressure delivered by valve 48. Turning cams 17 and 18 contact testing can 5 by rubber plates 30 and rotate with pins 19 and top holding plates 20 and 21 toward center of the testing can 5 until rubber plates 29 install on bodies 16 of sectional clamps 8 touch outside wall of the testing can 5. Angle of rotation turning cams 17 and 18 depend and control by outside diameter of testing can 5. Rotation stops and rubber plates 29 and 30 contacting the testing can 5 around. At the same time each top holding plates 20, 21 and 22 by chamfers 25 push the testing can 5 at outside area 26 down against Bellville spring 7. see FIGS. 3, 4. and 11). The Bellville spring 7 squeeze and the dome area 52 of testing can 5 stay fixed in vertical and horizontal positions. Distance between edges 27 of top holding plates 20, 21 and 22 and the stand 28 of testing can good enough for growth/buckle tests.

The sensor 31 installed by bracket on one side of the middle top holding plate 22 come to test area with sectional plates 8 and at first detect initial position of the stand 28 of the testing can 5 and send signal to PLC (do not shown). expandable rubber bushing 37. Inflation air pressure deliver through center hole 38 by valve 49 install on manifold 51 and distributed though cuts 33, pressing the testing can 5 vertically by outside area 26 of the testing can 5. Because force from air pressure push the testing can 5 at the same direction as force of Bellville spring 7 the testing can 5 continue stay in fixed vertical and horizontal positions. The each part of profile of the wall 44 expandable rubber bushing 37 stretched differently under inflation. The central part 45 is stretching at first and touch inside wall of the tested can 5. Upper 46 and lower 47 parts of the wall 44 expandable rubber bushing 37 turn by pressure in opposite directions, upper 46 is up and lower 47 is down. The shape create by inflation touch inside wall of testing can 5 make close chamber 34 which hold tests pressure. Level of air pressure for inflation of expandable rubber bushing 37 higher than tests pressure.

Growth air pressure deliver to through off side hole 36 by valve 50 installed on manifold 51. Air pressure for growth test increase maximum and check by pressure sensor (do not shown). The sensor 31 determine size of the maximum growth of the stand 28 and send signal to PLC (do not shown), the result will be shown, then air pressure will be release and some part of the growth of the testing can 5 return back. The sensor 31 will detect new position and send another signal to PLC (do not shown). Both signal (initial and last) will compare by PLC (do not shown) and result of residual part of the growth will show. Air pressure will increase again until the dome area 52 of the can 5 buckling. The pressure sensor (do not shown) is determining level of the testing pressure, the result will shown by PLC (do not shown) and an operator will determine quality of the testing can 5.

Cylinders 10 return sectional clamps 8 with bottom plates 9 used as the slides together with top holding plates 20, 21 and 22, with sensor 31 back. During return extension springs 24 turn turning cams 17 and 18 in open position. Doors 2 will open and the tested can 5 will be removed.

What is claimed is:

1. A growth/buckle tester device comprising:
   an expandable plug having a metal core with two holes for air delivery,
   a Bellville spring installed on top of the metal core with cut-outs around for test air delivery,
   an inflatable rubber bushing wherein a combination of the mechanical properties of the rubber, a special profile of a wall of the rubber bushing and the durometer of the rubber, which, when inflated, causes a central part of the inflatable rubber bushing to stretch in vertical and horizontal directions.

2. The growth/buckle tester device of claim 1, wherein test air pressure pushes the testing can in the same direction in which the Belleville spring expands allowing the growth/buckle tester device to test various sizes of cans currently produced, wherein said growth/buckle tester device does not require any additional replaceable parts, units (such as cylinders) and holding parts.

3. The growth/buckle tester device of claim 1, further comprising:
   a chamber wherein the chamber has a volume created by placing any one can selected from a plurality of differently sized cans that are currently produced to be tested by placing a dome area of the can on top of the Belleville spring, whereby needless air accumulation is avoided allowing the device to quickly compensate for differences of volume of air for different sizes of cans, thereby reducing the time required for the test and reducing dispersion of measurement values, thus making tests more accurate.

4. The growth/buckle tester of claim 1, further comprising:
   two sets of holding clamps, a respective set of holding clamps disposed on each side of a can to be tested, each set including the following parts:
   a fixed middle part having a top holding plate which is attached to body of the holding clamp and is attached to a rubber plate, wherein the rubber plate contacts the wall of the testing can;
   side parts including sectional turning cams with top holding plates, which turn with the sectional turning cams; and
   rubber plates, attached to the sectional turning cams, which are able to contact around cans of various diameters during the test, partially absorb inflated pressure and relieve a thin-walled tested can from the pressure, thereby increasing reliability and safety during the test.

5. The growth/buckle tester of claim 1 wherein the angle of rotation of the sectional turning cams is controlled by contacting the testing can during clamping.

6. The growth/buckle tester of claim 5 further comprising:
a sensor placed above the top holding plates of the middle body of the holding cams;
wherein the sensor is positioned precisely in a measurement area above a highest point of the dome of the can being tested by slides sliding together with the sectional turning cams, and wherein control of the location of the sensor is achieved by contacting the middle body of each of the holding clamps around the testing can.

7. The growth/buckle tester of claim 4 wherein each set of holding clamps further comprise a slide positioned on a bottom of each respective middle body for moving along a bottom plate via a respective guide disposed on the bottom plate on each side of the can being tested, the growth/buckle tester further comprising:
a cylinder with a predetermined stroke attached to the top of each respective slide for controlling the movement of each respective holding clamp, wherein the slides move on top of the bottom plate of the tester,
wherein each respective slide has holes on opposite sides of a can being tested with the distance between centers of a plurality of pairs of holes corresponding to half the length of the difference between diameters of pairs of differently sized cans that are currently produced,
wherein retractable spring plungers are installed on the guides and respectively engage with each hole, thereby correctly positioning the slides for the diameter of the can currently being tested.

\* \* \* \* \*